(12) United States Patent
Okuno

(10) Patent No.: US 11,311,254 B2
(45) Date of Patent: Apr. 26, 2022

(54) APPARATUS PHOTOGRAPHING APPARATUS

(71) Applicant: SHIMADZU CORPORATION, Kyoto (JP)

(72) Inventor: Tomoharu Okuno, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 59 days.

(21) Appl. No.: 16/631,318

(22) PCT Filed: May 2, 2018

(86) PCT No.: PCT/JP2018/017554
§ 371 (c)(1),
(2) Date: Jan. 15, 2020

(87) PCT Pub. No.: WO2019/064670
PCT Pub. Date: Apr. 4, 2019

(65) Prior Publication Data
US 2020/0163631 A1    May 28, 2020

(30) Foreign Application Priority Data
Sep. 27, 2017  (JP) .............................. JP2017-186054

(51) Int. Cl.
*A61B 6/00*      (2006.01)
*A61B 6/10*      (2006.01)

(52) U.S. Cl.
CPC ............ *A61B 6/102* (2013.01); *A61B 6/4452* (2013.01); *A61B 6/547* (2013.01); *A61B 6/586* (2013.01); *A61B 6/105* (2013.01); *A61B 6/4405* (2013.01); *A61B 6/461* (2013.01)

(58) Field of Classification Search
CPC ....... A61B 6/102; A61B 6/4452; A61B 6/547; A61B 6/586
See application file for complete search history.

(56) References Cited

U.S. PATENT DOCUMENTS

2007/0086570 A1* 4/2007 Spahn ................. A61B 6/4458
378/117

FOREIGN PATENT DOCUMENTS

| JP | 2006-055518 | 3/2006 |
|---|---|---|
| JP | 2011-139851 | 7/2011 |
| JP | 2014-079570 | 5/2014 |

(Continued)

OTHER PUBLICATIONS

PCT/JP2018/017554, International Search Report and Written Opinion dated Jul. 24, 2018, 8 pages—Japanese, 5 pages—English.

*Primary Examiner* — Dani Fox
(74) *Attorney, Agent, or Firm* — Andrew F. Young, Esq.; Nolte Lackenbach Siegel

(57) ABSTRACT

An acceleration sensor (10) is attached to a collimator (12) and detects an acceleration of the collimator (12), and a speed calculation unit that calculates the speed of the collimator 12 on a basis of the acceleration detected by the acceleration sensor (10). When the speed of the collimator (12) exceeds a setting speed that is set in advance, a lifting or lowering of an arm (13) is stopped by attaching a permanent electromagnet (42) to a stopper plate (43). In addition, a warning message as a warning indication is displayed on a display unit, and a warning sound as a warning indication is generated from a speaker. Accordingly, damage to an apparatus is prevented.

6 Claims, 11 Drawing Sheets

(56) References Cited

FOREIGN PATENT DOCUMENTS

| | | |
|---|---|---|
| JP | 5692412 | 2/2015 |
| JP | 6065248 | 1/2017 |

\* cited by examiner

APPARATUS PHOTOGRAPHING APPARATUS

CROSS REFERENCE TO RELATED APPLICATIONS

This application relates to, and claims priority from, Ser. No.: PCT/JP2018/017554 filed May 2, 2018, the entire contents of which are incorporated herein by reference, and which in turn claims priority from JP Ser. No.: JP2017-186054 filed Sep. 27, 2017.

FIGURE SELECTED FOR PUBLICATION

FIG. 3

BACKGROUND OF THE INVENTION

Field of the Invention

The present invention relates to a radiation imaging apparatus, such as an X-ray imaging apparatus, comprising a radiation irradiation element and a support mechanism supporting such a radiation irradiation element movably.

Description of the Related Art

The related art involves a movable (portable) X-ray imaging apparatus that performs X-ray imaging while moving from one patient's room to another patient's room equips an X-ray tube and a collimator as an X-ray irradiation element at the top of the arm liftable (movable up-and-down along the support column installed on the wheeled base) and is movable between patient's rooms with electric power provided by driving the motor installed to the wheeled base (Patent Document 1). According to such a movable X-ray imaging apparatus, the arm is lowered and fixed relative to the support column when being moved between patient's rooms. When the arm is under the condition of such a fixed position, the under surface of the arm is contacting with the fixing element called an arm catch. The pin installed to the under surface is housed inside a hole formed in the fixing element under such a condition. And when X-ray imaging is performed, an operator releases the fixing release bottom to unfix the fixed arm and lifts the arm together with the X-ray tube and the collimator to place such as the X-tube in the relevant position for X-ray imaging.

In addition, with regard to an X-ray imaging apparatus comprising a moving structure that supports and moves the X-ray irradiation element by the ceiling hanging type support mechanism, the tube moving mechanism of the X-ray irradiation element comprises the X-ray irradiation element having the X-ray tube, a horizontal moving element that moves horizontally the X-ray irradiation element in the X- and Y-direction orthogonal to each other and a hanging support element that moves up-and-down the X-ray irradiation element. The horizontal moving element comprises a rail installed on the ceiling surface and an aspect in which the hanging support element moves along the rail. And the hanging support element comprises an aspect in which the moving (traveling) along the rail suspends temporally at the predetermined position by a pin-stop mechanism installed to the rail (Patent Document 2).

Further, an X-ray imaging apparatus called a fluoroscopic imaging system or a popular X-ray imaging apparatus comprises the support mechanism that supports the X-ray irradiation element having the X-ray tube and the collimator and moves the X-ray irradiation element in the X-, Y-directions. And the end terminal of the moving stroke of the support mechanism comprises a mechanical stop mechanism that suspends the support mechanism.

RELATED PRIOR ART DOCUMENTS

Patent Document
Patent Document 1: JP Patent 6065248 B1
Patent Document 2: JP Patent 5692412 B1

ASPECTS AND SUMMARY OF THE INVENTION

Objects to be Solved

With regard to such an X-ray imaging apparatus, the X-ray irradiation element supported by the supporting mechanism functions to be movable in accordance with the operation by an operator. Therefore, when the X-ray irradiation element supported by the supporting mechanism moves with a high speed or big acceleration, the apparatus likely may be damaged.

For example, with respect to the movable X-ray imaging apparatus, the arm and the fixed element likely may be damaged. When the arm moves to be placed at the fixed element and the bottom surface of the arm or the pin set up thereon collides with the fixed portion at the high speed or big acceleration. In addition, with respect to the X-ray imaging apparatus having the ceiling hanging type supporting mechanism, the pin stop mechanism likely may be damaged when the supporting mechanism moves to the stop position at the high speed or big acceleration. Further, with regard to the other X-ray imaging apparatus, the mechanical stop mechanism may be damaged when the supporting mechanism collides with the mechanical stop mechanism of the moving stroke end terminal at the high speed or big acceleration.

The purpose of the present invention is to solve the above objects and to provide a radiation imaging apparatus capable of preventing the apparatus per se from damaging before taking place by detecting the incident occurred when the radiation irradiation element moves at the high speed or the big acceleration.

Means for Solving the Problem

According to one aspect of the present invention, a radiation imaging apparatus comprises: a radiation irradiation element; a supporting mechanism that movably supports the radiation irradiation element; an acceleration sensor that detects acceleration of the radiation irradiation element; and a moving control unit that controls moving of the radiation irradiation element based on the acceleration of the radiation irradiation element detected by the acceleration sensor.

According to one other aspect of the present invention, the radiation imaging apparatus further comprises a speed calculation unit that calculates a speed of the radiation irradiation element based on the acceleration of the radiation irradiation element detected by the acceleration sensor, wherein the moving control unit controls moving of the radiation irradiation element when the speed of the radiation irradiation element calculated by the speed calculation unit exceeds a predetermined value.

According to another aspect of the present invention, there is provided a radiation irradiation apparatus further comprising a position detection mechanism that detects the position of the radiation irradiation element, wherein the moving control unit controls moving of the radiation irradiation element based on the position of the radiation irradiation element detected by the position detection mechanism and the acceleration of the radiation irradiation element detected by the acceleration sensor.

According to another aspect of the present invention, there is provided a radiation irradiation apparatus further comprising the radiation irradiation element and the supporting mechanism that movably supports the radiation irradiation element further comprises the acceleration sensor that detects the acceleration of the radiation irradiation element and an alarm generation unit that generates an alarm based on the acceleration of the radiation irradiation element detected by the acceleration sensor.

According to another aspect of the present invention, there is provided a radiation irradiation apparatus further comprising a speed calculation unit that calculates a speed of the radiation irradiation element based on the acceleration of the radiation irradiation element detected by the acceleration sensor, wherein the alarm generation unit generates an alarm when the speed of the radiation irradiation element calculated by the speed calculation unit is over a predetermined value.

According to another aspect of the present invention, there is provided a radiation irradiation apparatus further comprising a position detection mechanism that detects a position of the radiation irradiation element, wherein the alarm generation unit control generates an alarm based on the position of the radiation irradiation element detected by the position detection mechanism and the acceleration of the radiation irradiation element detected by the acceleration sensor.

Effects of the Present Invention

According to another aspect of the present invention, there is provided the detail where a moving of the radiation irradiation element is controlled based on the acceleration of the radiation irradiation element detected by the acceleration meter, so that the damage of the apparatus can be prevented from occurrence.

According to another aspect of the present invention, there is provided the detail where a moving of the radiation irradiation element is controlled when the speed of the radiation irradiation element exceeds the predetermined value, so that the damage of the apparatus can be prevented from occurrence.

According to another aspect of the present invention, there is provided the detail where a moving of the radiation irradiation element is controlled based on the acceleration of the apparatus in the area where the apparatus is more likely to be damaged, so that the damage of the apparatus can be prevented from occurrence.

According to another of the present invention, there is provided the detail where an alarm is generated based on the acceleration of the radiation irradiation element detected by the acceleration meter, so that the damage of the apparatus can be prevented from occurrence.

According to another aspect of the present invention, the alarm is generated when the speed of the radiation irradiation element exceeds the predetermined value, so that the damage of the apparatus can be prevented from occurrence.

According to another aspect of the present invention, the alarm is generated based on the acceleration of the apparatus in the area where the apparatus is more likely to be damaged, so that the damage of the apparatus can be prevented from occurrence.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Figure 1:
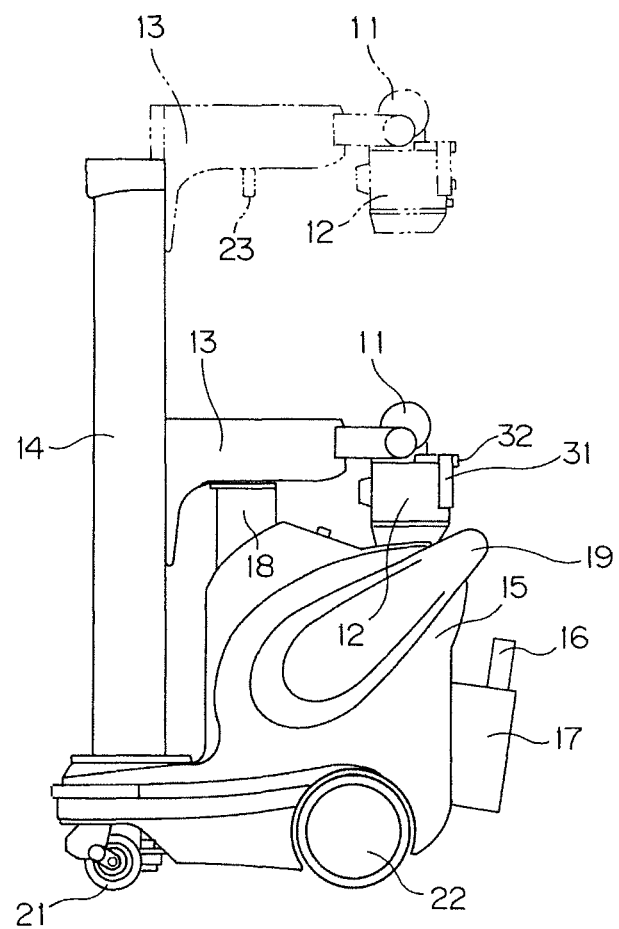
FIG. 1 is a schematic diagram illustrating the side view of an X-ray imaging apparatus according to an adaptive aspect of the present invention.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

It will be further understood by those of skill in the art that the apparatus and devices and the elements herein, without limitation, and including the sub components such as operational structures, circuits, communication pathways, and related elements, control elements, display circuits and display systems and elements, any necessary driving elements, inputs, sensors, detectors, memory elements, processors and any combinations of these structures etc. as will be understood by those of skill in the art as being capable of operating the systems and devices and subcomponents noted herein and structures that accomplish the functions without restrictive language or label requirements since those of skill in the art are well versed in related Radiation Photographing arts, computer and operational controls and technologies of radiographic devices and all their sub components, including various circuits and combinations of circuits without departing from the scope and spirit of the present invention.

Figure 2:
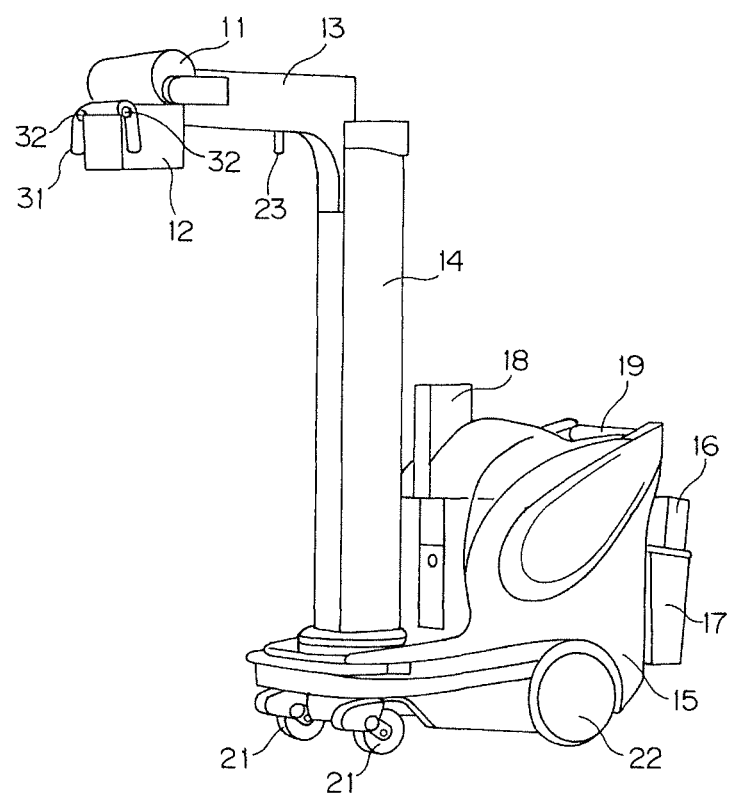
FIG. 2 is a perspective view illustrating an X-ray imaging apparatus according to one adaptive aspect of the present invention.

The inventor sets forth the aspects of alternative embodiments of the present invention based on the following FIGs.: FIG. 1 is a schematic diagram illustrating the X-ray imaging apparatus according to an alternative embodiment of the present invention, FIG. 2 is a perspective view illustrating an X-ray imaging apparatus according to an alternative embodiment of the present invention.

The X-ray imaging apparatus comprises: a supporting column 14 installed on the wheeled platform 15; an arm 13 that installed liftable relative to the supporting column 14; an X-ray tube 11 installed to the tip of the arm 13; a collimator 12 installed below the X-ray tube 11; an X-ray detector 16 that detects X-ray irradiated from the X-ray tube 11 and transmits through the subject; and a housing 17 that houses the X-ray detector 16. The X-ray irradiation element comprises the X-ray tube 11 and the collimator 12. In addition, the X-ray irradiation apparatus further comprises: a pair of right-and-left front wheels 21 that are wheels for changing the direction thereof; a pair of right-and-left rear wheels 22 that are wheels for driving; and an operation-handle 19 for operating the traveling direction of the wheeled platform 15.

Referring to FIG. 1, the arm 13 is liftable up-and-down between the fixed position, indicated by the solid line, where the arm 13 is in place when the wheeled platform 15 and the imaging position (lifted) higher than the fixed position. When the arm 13 is under the condition of such a fixed position, the under surface of the arm 13 is contacting with the fixing element 18 called the arm catch. The pin 23 installed to the under surface of the arm 13 is housed inside the hole (not shown in FIG.) formed in the fixing element 18 under such a condition. In addition, referring to FIG. 2, the arm 13 revolves around the supporting column 14 under the lifted condition from the fixed position.

The handle 31, which is used when the X-ray tube 11 and the collimator 12 are moved, is installed to the anterior of the collimator 12. And the handle 31 is equipped with a pair of release buttons 32 that unlocks fixing of the arm 13 by the fixing mechanism that prohibits the arm 13 from lifting and revolving. The collimator 12 comprises the acceleration sensor 10 (referring to FIG. 3 and FIG. 5) set forth later.

Figure 3:
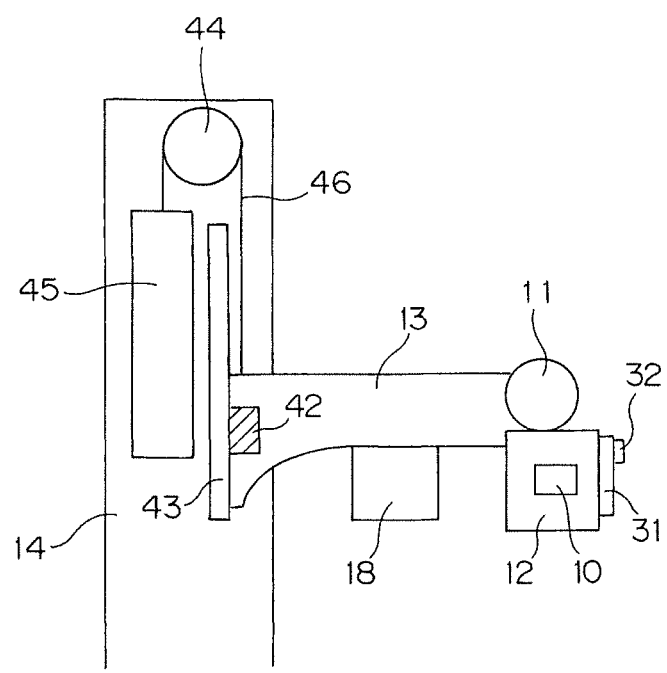
FIG. 3 is a schematic view illustrating an arm driving mechanism that lifts the arm 13 adopted in the X-ray imaging apparatus according to one adaptive aspect of the present invention and a fixing mechanism to fix the arm 13.

FIG. 3 is a schematic view illustrating an arm driving mechanism that lifts the arm 13 adopted in the X-ray imaging apparatus according to the aspect of Embodiment 1 of the present invention and a fixing mechanism to fix the arm 13.

The driving mechanism that lifts the arm 13 comprises a pulley 44 that is rotatably installed to the top of the inside of the supporting column 14, a counterweight 45 that is liftable up-and-down inside the supporting column 14, and a wire 46 that is winded the pulley 44 under the condition in which one end thereof is connected with the arm 13 and the other end is connected with the counterweight 45. The weight of the counterweight 45 is more or less the same as the total weight of the arm 13, the X-ray tube 11, the collimator 12 and so forth. A stopper plate 43 extending in the up-and-down direction is installed inside the supporting column 14. And a permanent electromagnet 42 is installed at the position facing the stopper plate 43 relative to the arm 13. Such a permanent electromagnet 42 functions as the fixing mechanism to fix the arm 13 at the position having a predetermined height.

Figure 4:
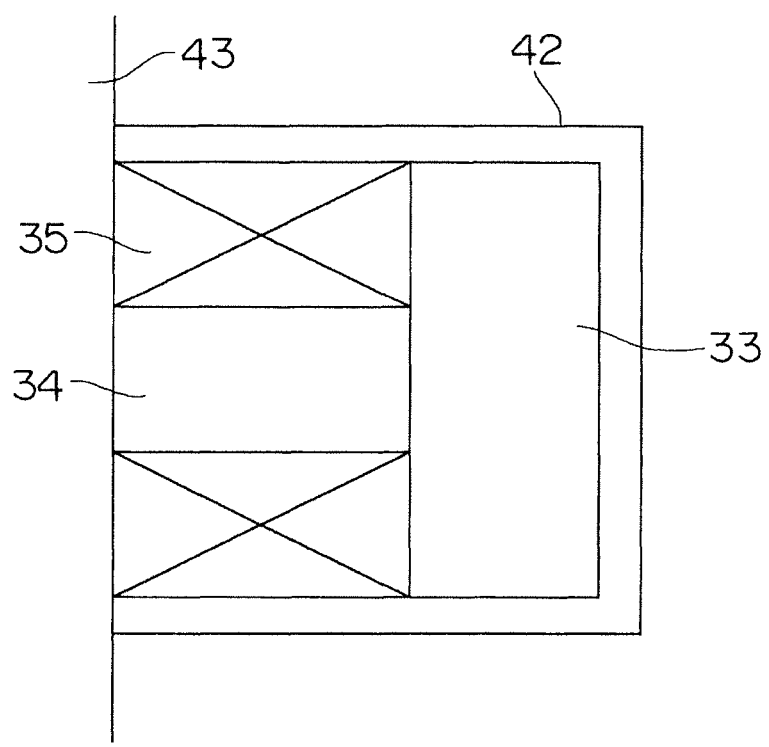
FIG. 4 illustrates a schematic view of a permanent electromagnet 42.

FIG. 4 illustrates a schematic view of a permanent electromagnet 42.

Such a permanent electromagnet 42 comprises a permanent magnet 33, an iron core 34 and a coil 35 winding the iron core 34. When no electric current runs the coil 35, such a permanent electromagnet 42 functions as a magnet due to the action of the permanent magnet 33. In such a case, the permanent electromagnet 42 adheres to the stopper plate 43, so that a breaking force is generated to limit moving of the arm 13. Whereas, when the operator adds the electric current to the coil 35 constituting the electromagnet by such as the operation for releasing the release button 32 and cancels to generate the magnetic force of the permanent magnet 33 relative to the electromagnet, the action of the permanent magnet 33 acts to release the breaking force and then, the arm 13 turns movable.

Figure 5:
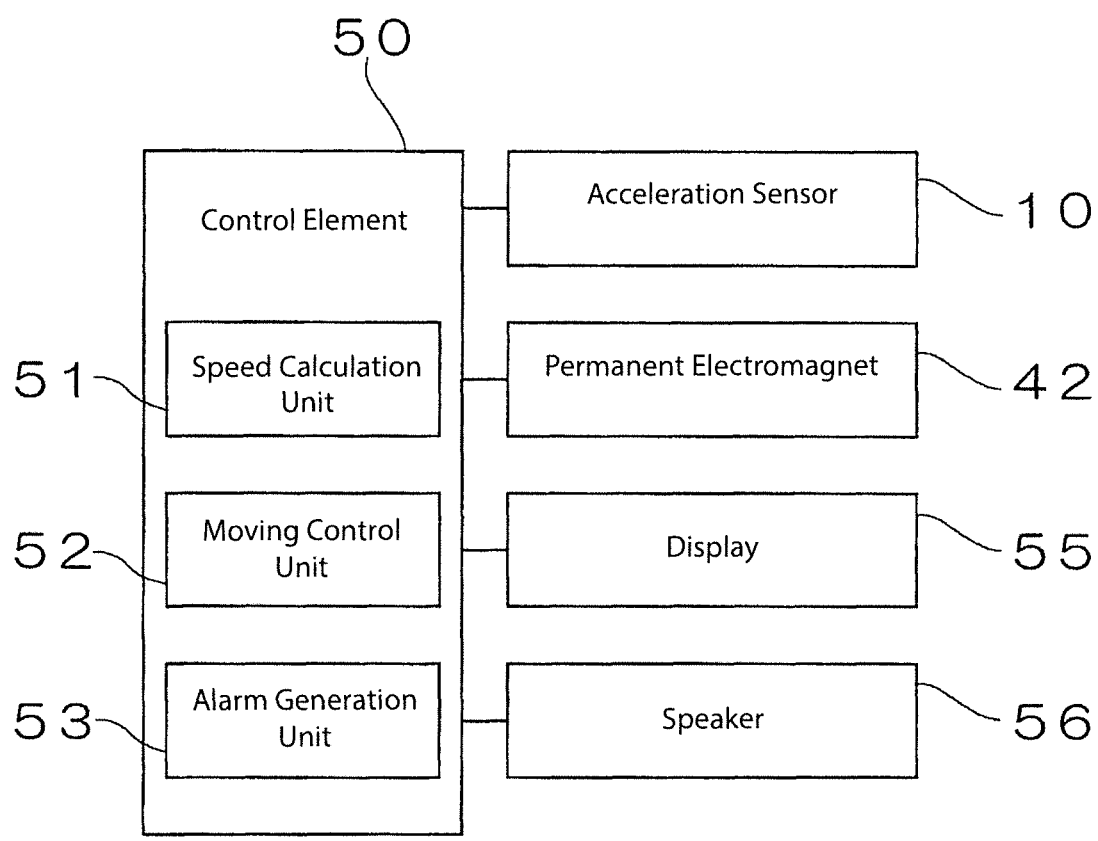
FIG. 5 is a block diagram illustrating the main control system of the X-ray imaging apparatus according to an aspect of the present invention.

FIG. 5 is a block diagram illustrating the main control system of the X-ray imaging apparatus according to an aspect of the Embodiment 1 of the present invention.

Such an X-ray imaging apparatus comprises a CPU that executes the logic operation as the processor, a ROM that stores operation programs required to control the apparatus, a RAM that stores temporally the data and so forth when controlling, and so forth and further comprises a control element 50 that controls the entire apparatus. Such a control element 50 comprises a computer in which software is installed. A function of each element included in the control element 50 is achieved by executing the software installed in the computer. As a functional component, such a control element 50 comprises a speed calculation unit 51 that calculates the speed of the X-ray irradiation element comprising the X-ray tube 11 and the collimator 12 by executing a cumulative calculation based on the acceleration of the radiation irradiation element detected by the acceleration sensor 10, a moving control unit 52 that rules moving of the X-ray irradiation element when the speed of the X-ray irradiation element that is calculated by the speed calculation unit 51 is over the predetermined value, and an alarm generation unit 53 that generates an alarm when the speed of the X-ray irradiation element that is calculated by the speed calculation unit 51 is over the predetermined value.

In addition, the control element 50 is also connected with the sensor 10 and the permanent electromagnet 42 set forth above. In addition, the control element 50 comprises a display 55 that displays a message as an alarm message directed by the alarm generation unit 53 and a speaker 56 that generates an alarm sound as the alarm representation directed by the alarm generation unit 53. Here, the display 55 can be a touch-panel display to operate the apparatus or a display exclusively for the alarm. In addition, an alarm lamp carries out alarming with light can be installed instead of the speaker 56 or together with the speaker 56.

With respect to the X-ray apparatus having the above configuration according to the aspect of Embodiment 1 of the present invention, the acceleration sensor 10 installed to the collimator 12 detects the acceleration of the collimator 12 when the operator moves the arm 13 up-and-down together with the X-ray tube 11 and the collimator 12 by operating the handle 31. The speed calculation unit 51 calculates the speed of the collimator 12 by executing the cumulative calculation based on the acceleration detected by the acceleration sensor 10.

And the moving control unit 52 sends a signal to the permanent electromagnet 42 to suspend lifting of the arm 13 by adhering the permanent electromagnet 42 to the stopper plate 43 when to the speed of the collimator 12 exceeds the predetermined setting speed. In addition, when the speed of the collimator 12 exceeds the predetermined setting speed, the alarm generation unit 53 sends a directive to the display 55 so that the display 55 displays an alarm message as the alarm display and also, sends a directive to the speaker 56 so that the speaker 56 generates the alarm sound therefrom.

As set forth above, with respect to the X-ray apparatus according to the aspect of the Embodiment 1, moving of the X-ray irradiation element is ruled and the alarm is generated when the speed of the X-ray irradiation element depending on the X-ray tube 11 and the collimator 12 exceeds the setting value, so that collisions, in which the bottom surface of the arm 13 or the pin 23 installed thereto collides with the fixing element 18 at high speed, can be prevented and as a result, the damage of the apparatus can be prevented.

Figure 6:
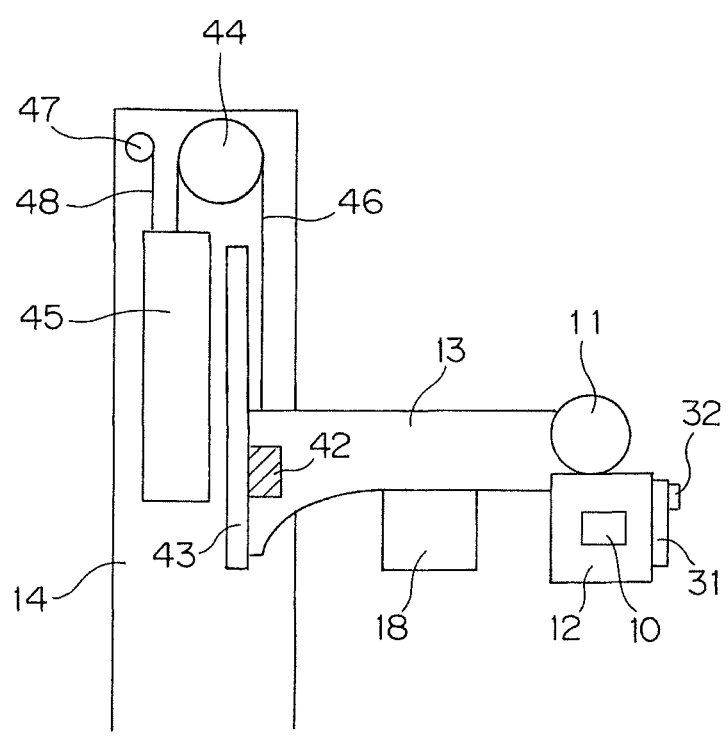
FIG. 6 is a schematic view illustrating an arm driving mechanism that lifts the arm 13 adopted in the X-ray imaging apparatus according to the aspect of Embodiment 2 of the present invention and a fixing mechanism to fix the arm 13.
Figure 7:
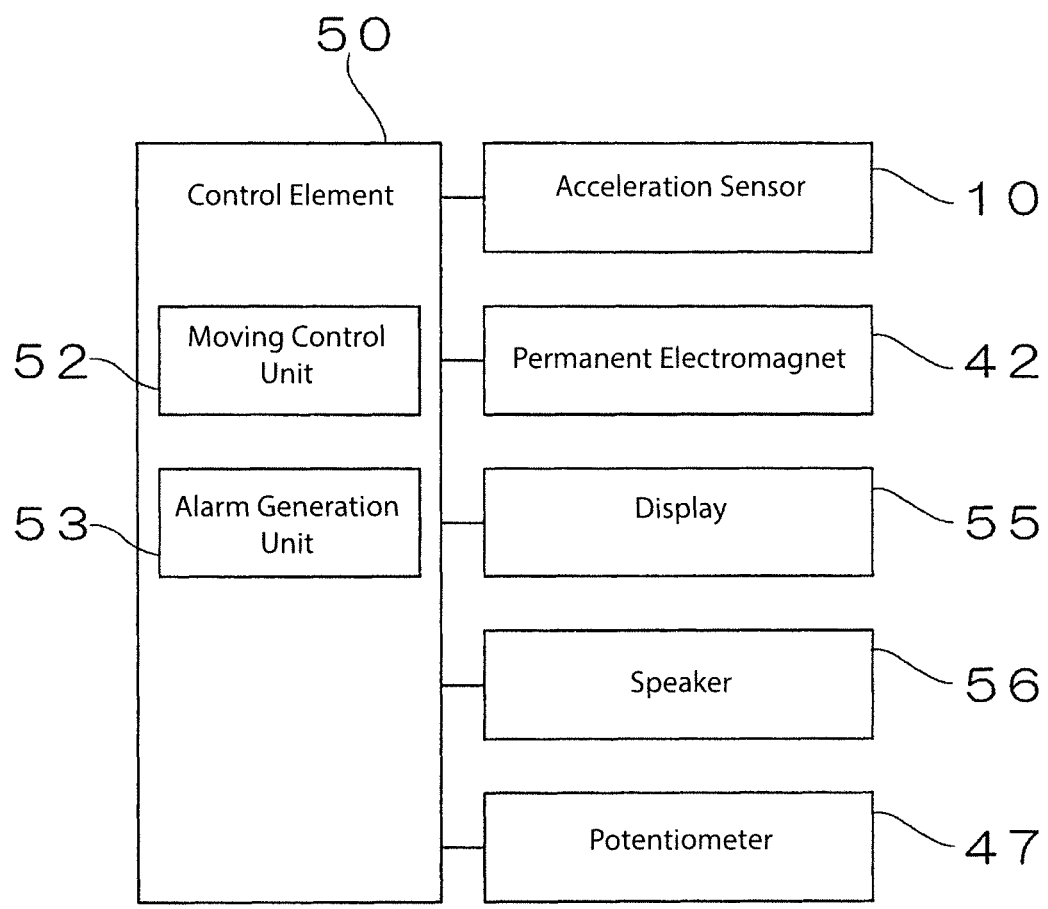
FIG. 7 is a block diagram illustrating the main control system of the X-ray imaging apparatus according to an aspect of the present invention.

Next, the inventor sets forth an alternative Embodiment of the present invention. FIG. 6 is a schematic view illustrating an arm driving mechanism that lifts the arm 13 adopted in the X-ray imaging apparatus according to the aspect of Embodiment 2 of the present invention and a fixing mechanism to fix the arm 13. In addition, FIG. 7 is a block diagram illustrating the main control system of the X-ray imaging apparatus according to the aspect of the Embodiment 2 of the present invention.

The aspect of the X-ray imaging apparatus according to the Embodiment 2 differs from the aspect of the Embodiment 1 as to the following points; that a potentiometer 47 is installed to detect the positional heights of the X-ray tube 11 and the collimator 12 that move up-and-down together with the arm 13; and that the speed calculation unit 51 that executes the cumulative calculation based on the acceleration of the radiation irradiation element detected by the acceleration sensor 10 is taken out.

Referring to FIG. 6, with respect to the X-ray imaging apparatus according to the aspect of the Embodiment 2, the counterweight 45 connects with the potentiometer 47 via the wire 48. The potentiometer 47 measures the positional heights of the arm 13 and the counterweight 45. And with respect to the X-ray imaging apparatus according to the aspect of the Embodiment 2, the moving of the X-ray irradiation element is ruled based on the position of the X-ray irradiation element detected using the potentiometer 47 and the acceleration of the X-ray irradiation element detected using the acceleration sensor 10 and the alarm is generated (in case).

Specifically, when the positional height of the arm 13 detected by the potentiometer 47 and the pin 23 installed to the bottom surface of the arm 13 are getting close to the fixing element 18, and the arm 13 is moving at the large acceleration, the arm 13 and/or the fixing element 18 may be damaged when the bottom surface of the arm 13 and the pin 23 installed thereto collides with the fixing element 18.

Therefore, with respect to the X-ray imaging apparatus according to the aspect of the Embodiment 2, when the positional height of the arm 13, which is detected by the potentiometer 47, is close to the fixing element 18 and the acceleration of the X-ray irradiation element detected using the acceleration sensor 10 is higher than the constant value, the moving of the arm supporting the X-ray irradiation element is ruled by the moving control unit 52 and the alarm generation unit 53 generates an alarm. Even when such a configuration is adopted, the bottom surface of the arm 13 or the pin 23 installed thereto is prevented from collision with the fixing element 18 at a high acceleration, so that the damage of the apparatus can be prevented.

Figure 8:
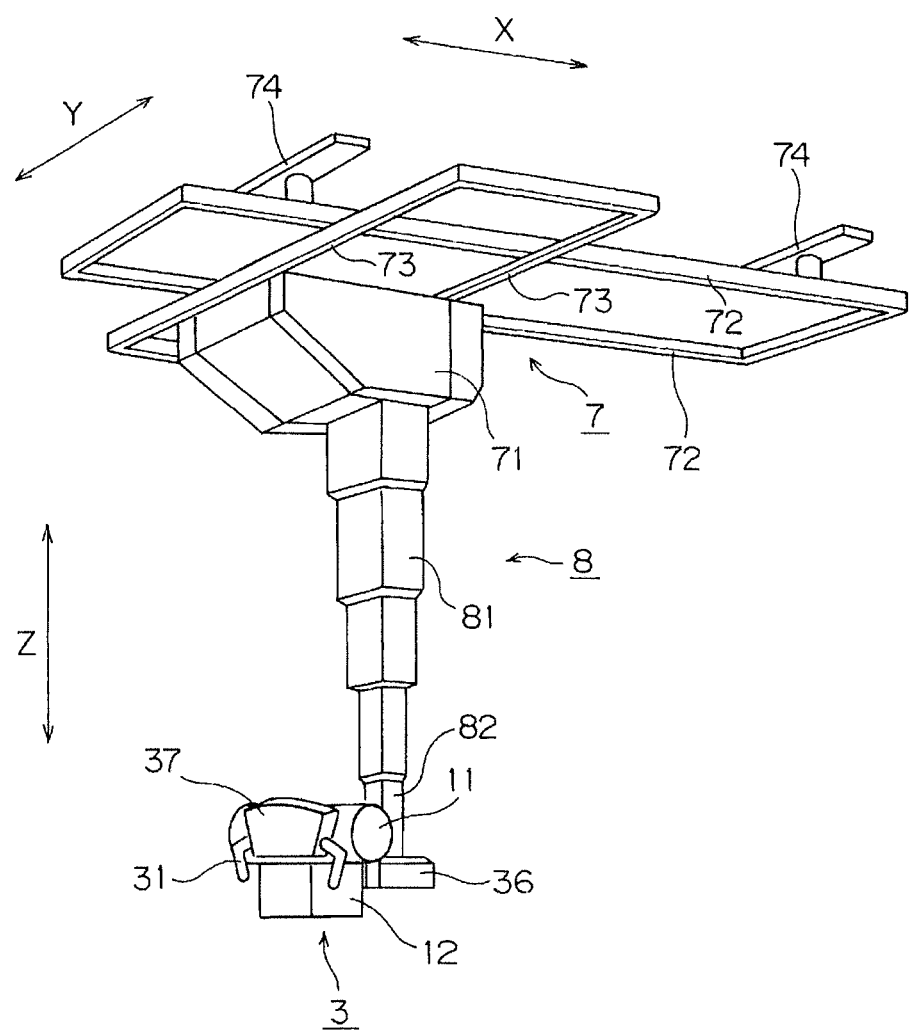
FIG. 8 is a perspective diagram illustrating the X-ray imaging apparatus according to another aspect of the present invention.
Figure 9:
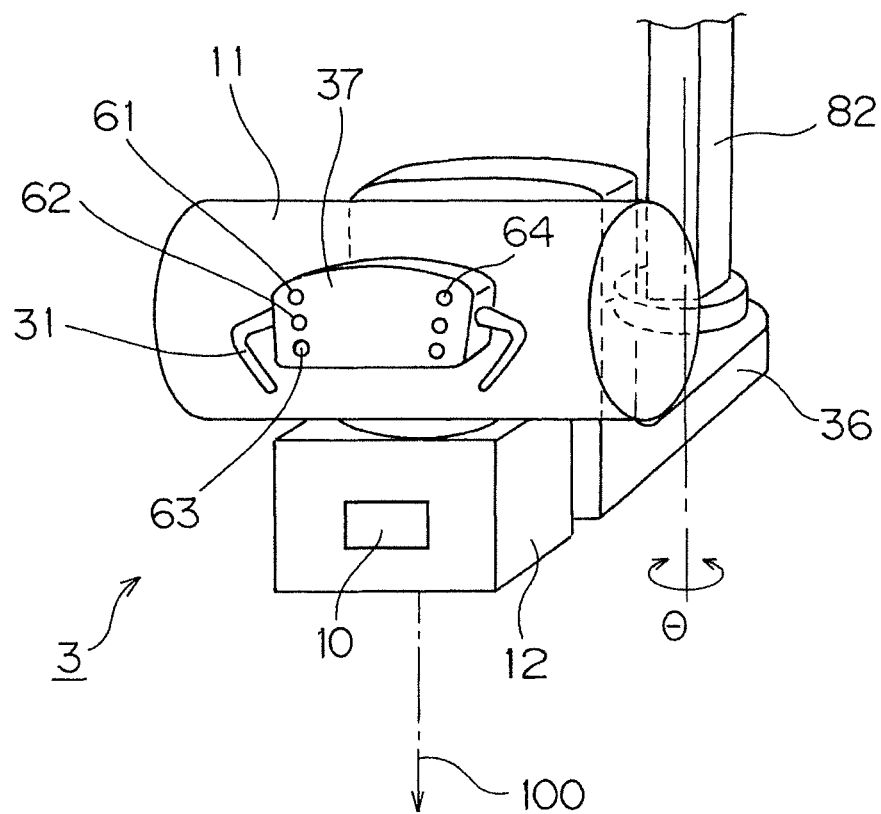
FIG. 9 is a perspective view illustrating the proximity of the X-ray irradiation element 3 of the X-ray imaging apparatus according to an aspect of the present invention.

Next, the inventor further sets forth another Embodiment of the present invention. FIG. 8 is a perspective diagram illustrating the principal elements of the X-ray imaging apparatus according to the aspect of the Embodiment 3 of the present invention. In addition, FIG. 9 is a perspective view illustrating the proximity of the X-ray irradiation element 3 thereof.

Such an X-ray imaging apparatus comprises the X-ray irradiation element 3 having the X-ray tube 11, the horizontal moving element 7 that moves horizontally the X-ray irradiation element 3 in the X- and Y-direction orthogonal to each other and a hanging support element 8 that moves up-and-down the X-ray irradiation element 3.

The horizontal moving element 7 comprises a pedestal 71 connected continuously with a hanging holding element 8, a pair of fixing rails 72 fixed to the ceiling surface via a pair of hanging elements 74, a pair of movable rails 73 movably connected along the fixing rails 72. The hanging holding element 8 connects with the pedestal 71 via the movable rails 73, wherein the pedestal 71 moves integrally together with the movable rails 73 in the moving direction along the fixed rails 72 (X-direction in FIG. 8) and movable along the movable rails 73 in the orthogonal direction (Y-direction in FIG. 8) to the moving direction along the fixed rails 72.

The hanging holding element 8 comprises a telescopic element 81 connected continuously with the pedestal 71 and a supporting column 82 installed to the bottom end of the telescopic element 81. Such a telescopic element 81 is capable of telescoping in the vertical direction (Z-direction in FIG. 8) and the X-ray irradiation element 3 is installed to the supporting column 82 at the bottom end of the telescopic element 81.

Referring to FIG. 9, the X-ray irradiation element 3 comprises a supporting block 36 rotatably installed in the 0 direction around the axis facing the vertical direction at the bottom end of the supporting column 82. The supporting block 36 comprises the X-ray tube 11, the collimator 12 and an operation panel 37 having a plurality of switches 61, 62, 63, 64 that further comprises a handle 31. Referring to FIG. 9, the radiation range of the X-ray irradiated from the X-ray tube 11 is limited by the collimator 12 and then, the radiation is irradiated to the subject as indicated by the two-dotted chain line 100. And referring to FIG. 9, the collimator 12 comprises the acceleration sensor 10.

Figure 10:
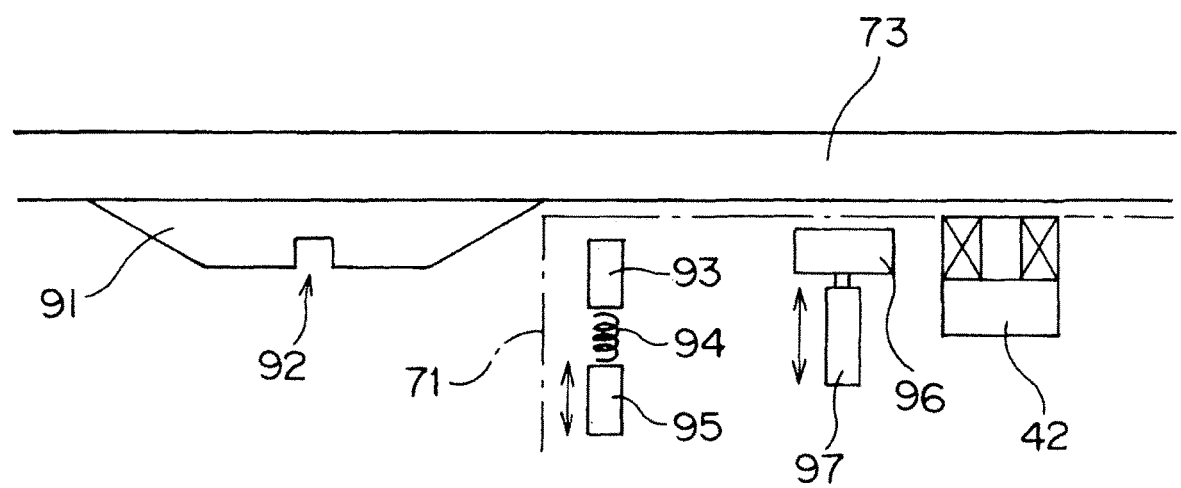
FIG. 10 is a schematic view illustrating the moving control mechanism of the X-ray imaging apparatus according to an aspect of the present invention.

FIG. 10 is a schematic view illustrating the moving control mechanism of the X-ray imaging apparatus according to an aspect of the Embodiment 3 of the present invention.

Referring to FIG. 10, the above movable rails 73 comprise a stop member 91 that configures the pin stop mechanism that suspends the moving of the X-ray irradiation element 3. Such a stop member 91 is made of a metal plate having the tilt surfaces formed on both sides of a concave element 92. In addition, the pedestal 71 connected continuously with the above hanging holding element 8 comprises a pin 93 connecting with the concave element 92 of the stop member 91, a break shoe 96 that provides the pedestal 71 with the breaking force by contacting with the movable rails 73, and the permanent electromagnet 42 referring to FIG. 4.

The pin 93 connects with a solenoid 95 via a spring 94. The pin 93 slides on the tilt surface of the stop member 91 in accordance with the action of the spring 94 and connects with the concave element 92 when the pedestal 71 moves toward the stop member 91. Then, the connective relationship between the pin 93 and the concave element 92 are removed in accordance with the action of the solenoid 95. In addition, the beak shoe 96 moves between the position at which connecting with the movable rails 73 and position at which leaving from the movable rails 73 in accordance with the action of the solenoid 97.

Figure 11:
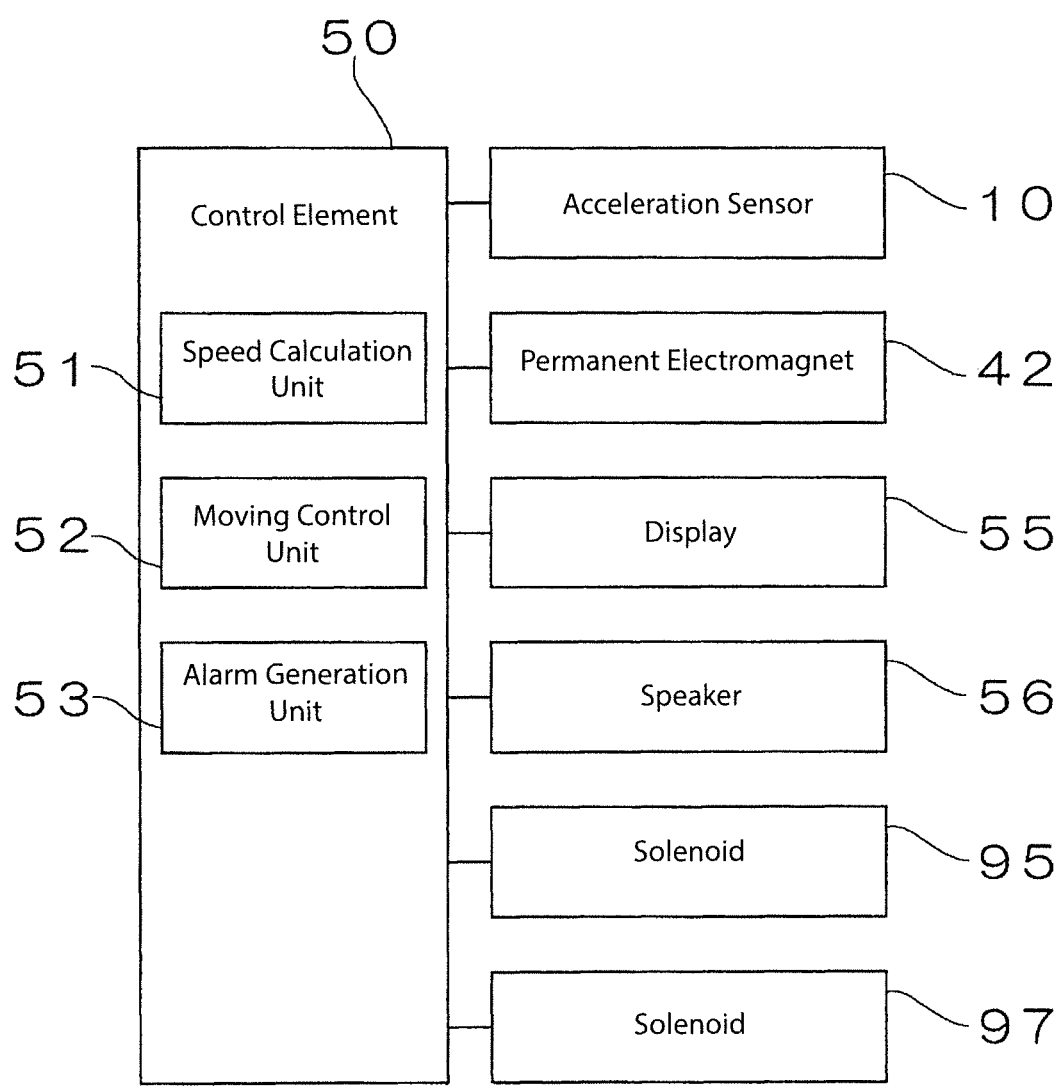
FIG. 11 is a block diagram illustrating the main control system of the X-ray imaging apparatus according to an aspect of the present invention.

FIG. 11 is a block diagram illustrating the main control system of the X-ray imaging apparatus according to an aspect of the Embodiment 3 of the present invention.

Such an X-ray imaging apparatus comprises the control element 50 as well as the X-ray imaging apparatus according to the aspect of the Embodiment 1. The control element 50 comprises a speed calculation unit 51. A moving control unit 52 and an alarm generation unit 53. In addition, the control element 50 is connected with such as the acceleration sensor 10, the permanent electromagnet 42, the display 55 and the speaker 56. Further, the control element 50 is connected with the solenoids 95, 97 as set forth above.

With respect to the X-ray apparatus having the above configuration according to the aspect of Embodiment 3 of the present invention, the acceleration sensor 10 installed to the collimator 12 detects the acceleration of the collimator 12 when the operator moves the X-ray irradiation element 3 comprising the X-ray tube 11 and the collimator 12 by operating the handle 31. The speed calculation unit 51 calculates the speed of the collimator 12 by executing the cumulative calculation based on the acceleration detected by the acceleration sensor 10.

And the moving control unit 52 first sends a signal to the solenoid 97 to provide the pedestal 71 with the braking force by contacting the movable rails 73 to the brake shoe 96 when the speed of the collimator 12 exceeds the predetermined setting speed. And then, the moving control unit 52 sends a signal to the permanent electromagnet 42 to suspend moving the pedestal 71 by adhering the permanent electromagnet 42 to the rail 73. In addition, in parallel, when the speed of the collimator 12 exceeds the predetermined setting speed, the alarm generation unit 53 sends a directive to the display 55 so that the display 55 displays an alarm message as the alarm display and also, sends a directive to the speaker 56 so that the speaker 56 generates the alarm sound therefrom.

Accordingly, the X-ray irradiation element 3 moves to the suspension position together with the horizontal moving element 7 and the hanging holding element 8 in a high-speed, so that the stop member 91 and the pin 93, which configures the pin-stop mechanism, can be prevented.

In addition, with respect to the X-ray imaging apparatus according to the aspect of the Embodiment 3, the control element 50 always recognizes a position of the pedestal 71 in the Y-direction. Accordingly, when the pedestal 71 is close to the stop member 91 and the pedestal 71 has been moving in a high-acceleration, as well as set forth above, steps of suspending moving the pedestal 71 by adhering the permanent electromagnet 42 to the movable rails 73, displaying the alarm message as the alarm display on the display 55 and generating an alarm sound as the alarm indication from the speaker 56 can be adopted following contacting the break shoe 9 to the movable rail 73 and providing the pedestal 71 with the breaking force so as to prevent the damage of the pin-stop mechanism.

In addition, as set forth above, the inventor sets forth the case in which executing such as restriction of moving based on the acceleration in the Y-direction along the movable rails 73 and also, in accordance with the same aspects, with respect to the X-direction along the fixed rails 72, moving is restricted based on the acceleration measured by the acceleration sensor 10 and the alarm is generated.

According to the aspect of any Embodiment set forth above, when the speed of the X-ray irradiation element, comprising the X-ray tube 11 and the collimator 12, exceeds the predetermined value, any one of the moving control unit 52 and the alarm generation unit 53 can be removed although the moving of the X-ray irradiation element is restricted by the moving control unit 52 and at the same time, the alarm generation unit 53 generates the alarm.

In addition, according to the aspect of any Embodiment set forth above, the acceleration sensor 10 can be placed in any position such as the X-ray tube 11 other than the collimator 12 as long as the position at which the acceleration of the X-ray irradiation element can be detected although the acceleration sensor 10 is installed to the collimator 12 in any Embodiment.

REFERENCE OF SIGNS

3 X-ray irradiation element
7 Horizontal moving element
8 Hanging holding element
10 Acceleration sensor
11 X-ray tube
12 Collimator
13 Arm
14 Supporting column
15 Wheeled platform
16 X-ray detector
18 Fixing element
23 Pin
42 Permanent electromagnet
43 Stopper plate
44 Pulley
45 Counterweight
46 Wire
47 Potentiometer
50 Control element
51 Speed calculation unit
52 Moving control unit
53 Alarm generation unit
55 Display
56 Speaker
71 Pedestal
72 Fixed rail
73 Movable rail
91 Stop member
93 Pin
95 Solenoid
96 Brake shoe
97 Solenoid Although only a few embodiments have been disclosed in detail above, other embodiments are possible and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. A radiation imaging apparatus, comprising:
  a radiation irradiation element;
  a supporting mechanism that supports said radiation irradiation element movably;
  an acceleration sensor that detects an acceleration of said radiation irradiation element when said radiation irradiation element moves; and
  a control element that compares said acceleration of said radiation irradiation element with a predetermined value of acceleration, said control element including:
    a moving control unit that rules moving of said radiation irradiation element when said acceleration detected by said acceleration sensor is higher than said predetermined value of acceleration.

2. The radiation imaging apparatus according to claim 1, further comprising:
  a position detection mechanism that detects a position of said radiation irradiation element; and
  wherein said moving control unit rules moving of said radiation irradiation element based on said position of said radiation irradiation element, detected by said position detection mechanism, and said acceleration of said radiation irradiation element detected by said acceleration sensor when said radiation irradiation element moves.

3. A radiation imaging apparatus comprising:
  a radiation irradiation element;
  a supporting mechanism that supports said radiation irradiation element movably;
  an acceleration sensor that detects an acceleration of said radiation irradiation element when said radiation irradiation element moves; and
  a control element that compares a speed of said radiation irradiation element with a predetermined value of speed, said control element including:
    a speed calculation unit that calculates said speed of said radiation irradiation element based on said acceleration of said radiation irradiation element, detected by said acceleration sensor; and
    a moving control unit that rules moving of said radiation irradiation element when said speed calculated by said speed calculation unit exceeds said predetermined value of speed.

4. A radiation imaging apparatus, comprising:
  a radiation irradiation element;
  a supporting mechanism that supports said radiation irradiation element movably;
  an acceleration sensor that detects an acceleration of said radiation irradiation element when said radiation irradiation element moves; and
  a control element that compares said acceleration of said radiation irradiation element with a predetermined value of acceleration, said control element including:
    an alarm generation unit that generates an alarm when said acceleration detected by said acceleration sensor is higher than said predetermined value of acceleration.

5. A radiation imaging apparatus, comprising:
  a radiation irradiation element;
  a support mechanism that supports said radiation irradiation element movably;
  an acceleration sensor that detects acceleration of said radiation irradiation element when said radiation irradiation element moves; and
  a control element that compares a speed of said radiation irradiation element with a predetermined value of speed, said control element including:
    a speed calculation unit that calculates said speed of said radiation irradiation element based on said acceleration of said radiation irradiation element, detected by said acceleration sensor; and
    an alarm generation unit that generates an alarm when said speed calculated by said speed calculation unit exceeds said predetermined value of speed.

6. The radiation imaging apparatus, according to claim 4, further comprising:
  a position detection mechanism that detects a position of said radiation irradiation element; and
  wherein said alarm generation unit generates an alarm based on said position of said radiation irradiation element, detected by said position detection mechanism, and said acceleration of said radiation irradiation element, detected by said acceleration sensor, when said radiation irradiation element moves.

* * * * *